United States Patent [19]
Stevenson

[11] Patent Number: 5,685,262
[45] Date of Patent: Nov. 11, 1997

[54] COLORIZING DISINFECTANT ESPECIALLY FOR MILK ANIMALS

[76] Inventor: Dale Vernon Stevenson, 940 Lake Shore Way, B-23, Lake Alfred, Fla. 33850

[21] Appl. No.: 431,789

[22] Filed: May 1, 1995

Related U.S. Application Data

[63] Continuation-in-part of Ser. No. 152,600, Nov. 15, 1993, Pat. No. 5,456,211, which is a continuation-in-part of Ser. No. 863,254, Apr. 2, 1992, Pat. No. 5,261,353, which is a continuation-in-part of Ser. No. 608,918, Nov. 5, 1990, Pat. No. 5,101,770.

[51] Int. Cl.$^6$ ................................................ A01K 29/00
[52] U.S. Cl. .................. 119/651; 119/665; 424/10.3; 424/665
[58] Field of Search ........................... 119/156–160

[56] References Cited

U.S. PATENT DOCUMENTS

| | | | |
|---|---|---|---|
| 4,693,832 | 9/1987 | Hurst | 210/756 |
| 5,236,595 | 8/1993 | Wang et al. | 210/669 |

*Primary Examiner*—Thomas Price
*Attorney, Agent, or Firm*—Charles A. McClure

[57] ABSTRACT

Disinfectant with colorizer as positive visual indicator of its application to skin, such as udders of milking animals, especially those whose milk production is BST-stimulated, to preclude mastitis. Iodine-free aqueous solution of a permanganate as colorizer and a hypochlorite as disinfectant, buffered to pH of 9 to 10, is applied to udder, especially to the teats, in post-milking step. Removal of residual color is enabled by acidic peroxide solution also similarly useful to decolorize any permanganate-colored animal or human skin.

20 Claims, 1 Drawing Sheet

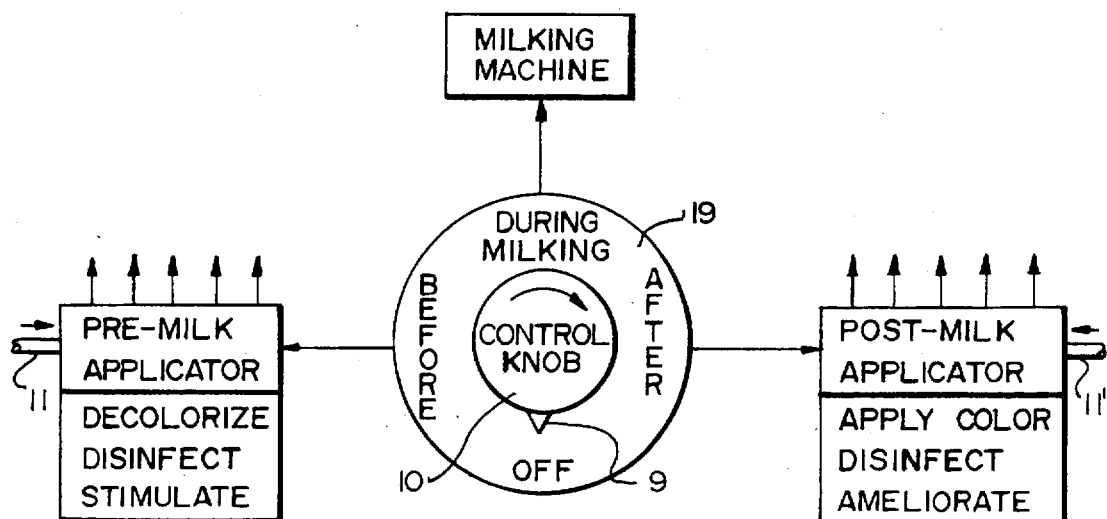
FIG. 1
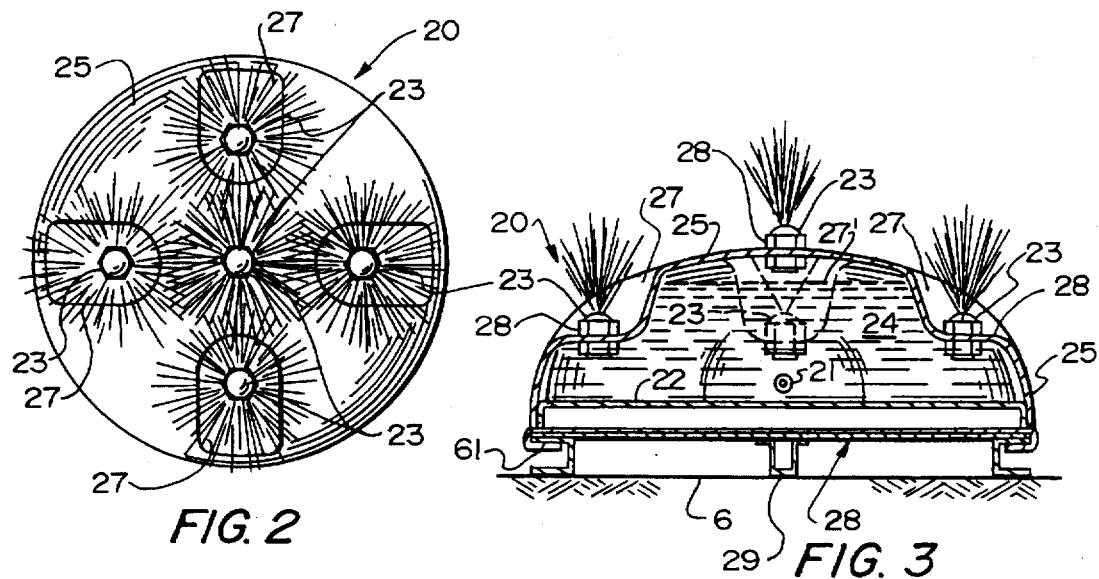
FIG. 2
FIG. 3
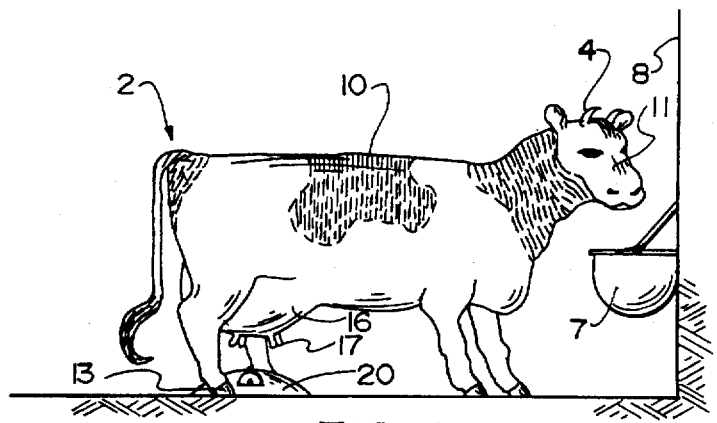
FIG. 4

COLORIZING DISINFECTANT ESPECIALLY FOR MILK ANIMALS

This is a continuation-in-part of my patent application, Ser. No. 08/152,600, filed Nov. 15, 1993, now U.S. Pat. No. 5,456,211, which was a continuation-in part of my application Ser. No. 07/863,254, filed Apr. 2, 1992, now U.S. Pat. No. 5,261,353; which was a continuation-in-part of my application Ser. No. 07/608,919, filed Nov. 5, 1990, now U.S. Pat. No. 5,101,770; incorporated by this reference.

TECHNICAL FIELD

This invention relates to udder care of domestic animals milked for human benefit, especially compositions and methods of disinfecting the udder, including the teats, to safeguard against infection, including visual indication of disinfectant application.

BACKGROUND OF THE INVENTION

Sanitation in food preparation is usually principally for the direct benefit of the consumer, but where the food is produced by a living animal, as in the instance of milk, it is also desirable to safeguard the health of the animal—as well as the product output rate or quantity and its condition—by taking suitable sanitary precautions. The udder and particularly the teats of milk animals are highly susceptible to infection from contact with flies, manure, people's hands, etc., so good milking technique includes application of suitable disinfecting compositions.

Recent introduction of bovine somatotropin (BST) accentuated the latter need, as the resulting increase in milking duration and/or frequency is conducive to further susceptibility to and/or incidence of mastitis. The rise in output per milk animal treated with BST requires enhanced udder and teat cleanliness of the milk animals upon which such demands for increased output are being made.

For many years the preferred germicide in disinfectants for such use has been iodine, which in elemental form is not soluble in water (though some of its salts and other combined forms are) but is soluble in alcohol and many other organic liquids. Its traditional popularity with dairymen stems in part from the characteristically intransigent stain it leaves as visible evidence of its application.

However, iodine and its customary liquid formulations foster chapping and cracking, which not only are painful but also provide new sites for infection. Iodophoric compositions advanced as less troublesome are found in these representative U.S. Pat. Nos.: Hall 3,663,694 (ethoxylated lanolin), Eckols 4,012,504 (mineral oil, with polyoxyethylene cetyl ether), Foll et al. 4,288,428 (alkylphenoxy-poly [ethyleneoxy]ethanol or polyvinylpyrrolidone), and Lauermann et al. 4,466,959 (glycerin, paraffin oil, and higher fatty acids).

Such efforts suggest that there is a need for further improvements in this art, preferably a new departure rather than simply more—or more varied—iodophors, and other germicides have been made the basis of disinfectants for udder treatment. The efficacy of chlorine-containing compositions, e.g., common hypochlorite solution ("Clorox") is reported in *Journal of Dairy Science*, vol. 56, no. 1, p. 148 (January 1973) and references cited therein. However, they have not been generally accepted, regardless of efficacy—in part because of tradition, and in part because of lack of coloration to assure positive monitoring that the treatment has been accomplished.

Lasting colorizers of hypochlorite bleaches used for different purposes also are identified in such U.S. Pat. Nos. as Kitchen et al. 3,544,373 (phthalocyanines), Hung 4,536,367 (triphenylmethanes), and Sudbury 4,457,855 (anthraquinones), for example. However, they are not suitable for the present purpose because of their persistence.

Prince U.S. Pat. No. 3,950,554, while urging the use of a fatty acid ester plus drying oil to form a water-resistant film on udders, included a suggestion of an edible organic dye, such as carotene, as well as hypochlorites, iodophors, and/or other udder disinfectants. His teachings failed to make any appreciable impression on the art, at least in the direction suggested above as desirable.

SUMMARY OF THE INVENTION

A primary object of the present invention is to ascertain that udders of milking animals, especially those being treated with BST are subjected to timely disinfection, plus color indication thereof.

Another object of this invention is to ameliorate the undesired side-effects characteristic of iodophoric disinfection of udders.

A further object of the present invention is to include visible coloration with udder disinfectant application to milk animals, preferably promptly after milking, as an indicator of disinfection.

Yet another object of this invention is provide a decolorizing option useful wherever udder coloration lasts until next milking, or alternatively a decolorizing pre-milking udder treatment if needed, also useful to decolorize hands of persons caring for milk animals.

A still further object is to attain the foregoing and related objects efficiently and economically, without resorting to iodine, non-aqueous liquids, organic dyes, or any complex expensive means.

In general, the objects of the present invention are attained, in a post-milking disinfecting step producing a coloration effective to indicate that the disinfectant has been applied to the udder and particularly to the teats. Decolorizing, preferably also disinfecting, at the next pre-milking is optionally available just as simply. Such decolorizing is equally effective upon the hands of handlers of milk animals or other human or animal skin colored by permanganate.

More particularly, according to this invention, at post-milking a coloring disinfecting step is performed, as by dipping or spraying the teats with a hypochlorite solution colored with a permanganate. If the color is persistent at pre-milking, a decolorizing and disinfecting step is performed with a peroxide/organic acid mixture.

Other objects of the present invention, together with means and methods for attaining the various objects, will be apparent from the following description and accompanying diagrams of preferred embodiments, which are presented by way of example rather than limitation.

SUMMARY OF THE DRAWINGS

FIG. 1 is a schematic diagram of apparatus useful in practicing this invention;

FIG. 2 is a plan view of applicator apparatus similarly useful;

FIG. 3 is a side elevation of the apparatus of FIG. 2; and

FIG. 4 is a side elevation of such apparatus, reduced in scale, and with a milk animal shown appropriately positioned above it.

DESCRIPTION OF THE INVENTION

FIG. 1 shows schematically control knob 10 (curved arrow shows setting order) plus pointer 9 and scale 19, with four positions at main compass points marked BEFORE (west), DURING (north), and AFTER (east) MILKING, and OFF (south). A north arrow designates a MILKING MACHINE conveniently actuatable by the control knob. Such a machine may (and usually would) be conventional in design and operation, may be actuated separately instead of by such knob, and is not shown or described because it may even be omitted as not being a part of this invention—which is compatible with performance of milking by hand.

Arrows to the west and east scale positions designate PRE-MILK and POST-MILK applicators, respectively, either a single device used to apply respective compositions sequentially, or optionally distinct devices each dedicated to applying its particular composition. Tubes 11, 11' suggest liquid supply to the respective applicators. Short arrows pointing up from each applicator block are suggestive of their function in applying liquid upward to an overlying udder. Blocks under the respective applicator blocks list their functions: the PRE-MILK method steps, DECOLORIZE, DISINFECT, and STIMULATE; and the POST-MILK method steps, APPLY COLOR, DISINFECT, and AMELIORATE. These functions are considered further in method terms hereinafter.

FIGS. 2 and 3 show in plan and in side elevation, respectively, applicator 20 suited to the practice of the present invention. Such applicator, shown here by way of example, is further illustrated and described by Belden in U.S. Pat. No. 3,554,166. Flat circular base plate 28 rests on feet 29 underlying it at the compass points and supports reinforcing envelope 22 over its entire upper surface. The envelope in turn is overlain by domed cover 25. Nozzle cavities 27 are recessed around five nozzles 23 directed upward from individual apertures 28 in the domed cover, within four respective nozzle cavities 27 recessed in the cover at quadrantal intervals about the center, and one at the dome center 27'. Compartment 24 formed between the cover and the envelope is shown containing the appropriate liquid received through pipe 21 from an external source (not shown).

FIG. 4 shows inside elevation, milk cow 30 in milking stall 32 defined by floor 31 supporting the cow and by wall 38 supporting feed container 37, which aids in orienting the cow therein so that applicator 20 underlies overhanging udder 36 with teats 34. Rear hooves 33 (one visible) of the cow flank the applicator, whose sloping domed cover is unlikely to have a hoof stand thereon even though the applicator is resting on the floor as shown. The floor is an alternative to a dolly or trolley (which may be employed instead, if preferred) and leaves plenty of space to swing the teat cups and connecting tubes of a milking machine (not shown) into an appropriate position. The illustrated apparatus is shown by way of explanatory working apparatus example. Similar or other means may be employed to apply either the POST-MILK colorizing disinfecting composition or the optional PRE-MILK application, but any such other apparatus is omitted here in the interest of simplicity of illustration.

Operation of the illustrated apparatus to practice the method of this invention is readily understood from the foregoing diagrams, the accompanying description, and these remarks. For simplicity it is assumed that only one applicator is used to spray the treating composition, pumped under sufficient force, appropriately upward and onto the overhanging udder. Any excess liquid will drip onto the applicator and from there to the floor or to the floor directly and flow to a drain (not shown) or be absorbed by material on the floor.

The POST-MILK solution comprises hypochlorite preferably plus a suitable buffer to a pH of about 9 to 10, and a coloring amount (at least a trace) of permanganate. The first and last ingredients are both alkali metal compositions, preferably sodium hypochlorite and potassium permanganate, whereas the buffer is preferably organic. Several percent hypochlorite to a maximum of about five percent by weight preferably with a few tenths percent of acetic acid in the form of vinegar, and a trace of permanganate, should suffice. All erstwhile chemistry students recognize the persistent characteristic purplish brown stain of permanganate. Emollients, such as lanolin, may be added to ameliorate effects of milking and of frequent application of disinfectants upon the udder.

As an preparation example, permanganate granules can be suspended within a porous membrane in a given volume of water for a given period of time or to a desired degree of coloration, with or without stirring. With moderate circulation, an hour should suffice for an ounce of potassium permanganate in a gallon of water. The water, which takes on a permanganate color, is decanted off into an appropriate aqueous hypochlorite solution of known volume. The color is conveniently controllable by adjusting either the permanganate perfusion time or the ratio of dilution (or both). With the suggested time, moderate dilution such as nine or ten times the volume of the colored water suffices for an intermediate duration of udder coloration. To be assured of color persistence to the next milking, at most half such ratio is preferable. To assure that a decolorizing step will be superfluous, at least about twice such dilution ratio is recommended. Solution color can be checked either by eye or by colorimeter, but a better empirical guide is the actually observed udder coloration under specific environmental conditions in a particular dairy herd, which can be taken into account in varying or customizing the formulation method appropriately.

Moderate single-digit concentrations of sodium hypochlorite are effective to produce the desired antimicrobial action. Double-digit percentages are harmful as too caustic (pH 11 to 12). From about 4.5 to 5.5% hypochlorite is preferred, although the range from at least several to at most about a half dozen percent may be considered so long as the pH is held at about 9 to 10. Dilute organic acid, such as aqueous acetic, readily available in vinegars, is useful in moderating an excessive pH to the desirable range. The colorizing solution can be monitored while adding such a buffer to produce a cool-weather pH of about 9 or warm-weather pH of about 10.

The concentration of permanganate can be varied, depending upon how long the indication is desired to persist. A permanganate-stained udder shows at a glance that it was treated with disinfectant. Optionally one or more lanolin-based or other emollients may be added to ameliorate harsh effects of frequent milking, etc.

Such POST-MILK treatment is more efficacious against microbial agents harmful to milk animals and potentially harmful to humans than any iodine or iodophoric compositions tolerable to them. It is especially well received where the animals' milk production is being stimulated by treatment with bovine somatotropin (BST) composition.

The optional PRE-MILK solution comprises about several percent each of peroxide and lower aliphatic acid. Suitable examples and preferred by experience are hydrogen peroxide and acetic acid. Such solution may be formulated by adding vinegar to aqueous hydrogen peroxide at dilute strength available in drugstores. Alternatively, a corresponding lesser amount of higher strength hydrogen peroxide solution readily available commercially can be diluted accordingly. The end solution has both disinfecting qualities and decolorizing capability as considered further below. Spraying it vigorously onto the udder is conducive not only to decolorization but also to the ensuing milking as it stimulates the animal to "let down" the milk.

If appreciable color remains on the udder as the time for next milking approaches, a decolorizing PRE-MILK session may be held. Upon application, the acidic solution of hydrogen peroxide converts the permanganate to the colorless manganate and releases oxygen gas of twice the volume available from the hydrogen peroxide, providing a strong supplementary disinfecting action. The clean udder is then ready for milking, and after such intervening milking is subjected again to permanganate colorizing again at a POST-MILK session.

Either application procedure can be accomplished manually by dip cup, given the appropriate compositions, but a semi-automated procedure is preferable. Other apparatus may be used in like manner with appropriate adaptation to the inventive method. Spray outlets different in number and orientation from those shown may be substituted, with or without additional desirable features.

Advantages and benefits of the apparatus and the method of this invention have been mentioned and are readily recognizable. Others doubtless will accrue to persons who practice the invention—and to the animals upon which they practice it.

Preferred embodiments and variants have been suggested for this invention. Other modifications may be made, deleting, or subdividing deleting, or subdividing compositions, parts, or steps, while retaining all or some of the advantages and benefits of the present invention—which itself is defined in the following claims.

The invention claimed is:

1. An iodine-free aqueous antimicrobial composition adapted to disinfect an udder of a milk animal, whose milk production may be somatotropin-stimulated, and to color it for at least a part of the time between successive milkings, comprising an aqueous disinfectant having a pH between about 9 and 10, including compatible colorizer.

2. The composition of claim 1 wherein the disinfectant comprises a hypochlorite.

3. The composition of claim 2, including an organic buffer.

4. The composition of claim 2 wherein the colorizer comprises a permanganate.

5. The composition of claim 1, wherein the disinfectant comprises an alkali metal hypochlorite, and the colorizer comprises an alkali metal permanganate.

6. An iodine-free aqueous antimicrobial composition adapted to disinfect an udder of a milk animal, whose milk production may be somatotropin-stimulated, and to color it for at least a part of the time between successive milkings, comprising an aqueous hypochlorite disinfectant buffered to a pH between about 9 and 10, including a compatible inorganic colorizer.

7. The composition of claim 6, comprising alkali metal hypochlorite as the disinfectant buffered by a weakly acidic organic composition.

8. The composition of claim 6, comprising an alkali metal permanganate as colorizer in amount effective to color udders by contact with the antimicrobial composition containing it.

9. The composition of claim 6, comprising an aqueous solution at least several percent and at most a half dozen percent by weight of sodium hypochlorite.

10. The composition of claim 6, comprising potassium permanganate as colorizer in amount effective to color udders by contact with the antimicrobial solution containing it, and adapted to be removed therefrom by application of weakly acidic aqueous peroxide.

11. Method comprising disinfecting the udder of a milk animal with the aqueous composition of claim 6, wherein the fact of such disinfecting treatment is indicated by resulting udder coloration, including applying the composition to the udder by at least one of the following steps: (i) spraying the composition onto the udder, (ii) dipping the udder into the composition.

12. Method according to claim 11, including the step of performing the disinfecting and coloring as a pre-treatment, just before milking.

13. Method according to claim 11, including the step of performing the disinfecting and coloring as a post-treatment, just after milking.

14. Method according to claim 11, including the steps of performing the disinfecting and coloring as a pre-treatment, just before milking, and also performing the disinfecting and coloring as a post-treatment, just after milking.

15. Method according to claim 11, including an added step of removing the indicating color by applying weakly acidic aqueous peroxide to the udder after the disinfecting coloring treatment.

16. Method according to claim 11, performed on a milk animal whose production is being somatotropin-stimulated.

17. For application to animal or human skin, a disinfectant indicator, comprising an iodine-free colorizing disinfectant containing a hypochlorite as disinfectant and a permanganate as colorizer; the purplish resulting indicating color being persistent but removable by subsequent application of a weakly acidic aqueous peroxide solution.

18. The composition of claim 17, containing sodium hypochlorite as disinfectant buffered to a pH of about 9 to 10 and potassium permanganate as colorizer to desired degree and duration.

19. Method including the step of applying the disinfecting and coloring composition of claim 18 to selected human or animal skin.

20. Method according to claim 19, including the step of removing color from the skin, after the disinfecting coloring treatment, by applying weakly acidic aqueous peroxide thereto.

* * * * *